United States Patent
Ouzounov

(10) Patent No.: US 11,506,770 B2
(45) Date of Patent: Nov. 22, 2022

(54) ULTRASOUND IMAGING SYSTEM PROBE AND SYSTEM, AND AN IMAGING METHOD

(71) Applicant: KONINKLIJKE PHILIPS N.V., Eindhoven (NL)

(72) Inventor: Sotir Filipov Ouzounov, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 922 days.

(21) Appl. No.: 15/780,250

(22) PCT Filed: Dec. 9, 2016

(86) PCT No.: PCT/EP2016/080409
§ 371 (c)(1),
(2) Date: May 31, 2018

(87) PCT Pub. No.: WO2017/097968
PCT Pub. Date: Jun. 15, 2017

(65) Prior Publication Data
US 2018/0348349 A1 Dec. 6, 2018

(30) Foreign Application Priority Data
Dec. 10, 2015 (EP) .................... 15198841

(51) Int. Cl.
*G01S 7/52* (2006.01)
*A61B 8/08* (2006.01)
(Continued)

(52) U.S. Cl.
CPC .......... *G01S 7/52046* (2013.01); *A61B 8/065* (2013.01); *A61B 8/42* (2013.01);
(Continued)

(58) Field of Classification Search
CPC ........ G01S 7/52; G01S 15/89; G01S 7/52046; G01S 7/5208; G01S 7/52092;
(Continued)

(56) References Cited

U.S. PATENT DOCUMENTS 4,691,571 A * 9/1987 Matzuk ............... G01S 7/52025
73/632
5,565,868 A  10/1996 Azrouf et al.
(Continued)

FOREIGN PATENT DOCUMENTS

JP 2007082806 A 4/2007
WO 2015028945 A2 3/2015

OTHER PUBLICATIONS

Lisheng; A 1.8 V CMOS fourth-order Gm-C bandpass sigma-delta modulator dedicated to front-end ultrasonic receivers, Analog Integrated Circuits and Signal Processing, Kluwer Academic Publishers, BO, vol. 48, No. 2, May 9, 2006 (May 9, 2006), pp. 121-132, XP019390181, ISSN: 1573-1979, DOI: 10.1007 (Year: 2006).*
(Continued)

*Primary Examiner* — Isam A Alsomiri
*Assistant Examiner* — Amie M NDure

(57) ABSTRACT

An ultrasound imaging system probe comprises an imaging transducer head and a reception circuit for processing received reflected ultrasound signals. The reception circuit comprises an analogue to digital sigma delta converter which comprises a closed loop which comprises a tunable band pass filter. This enables the analog to digital converter to process only the desired frequency band. The ADC conversion bandwidth and ENOB are in this way programmable giving a more efficient probe design, and also enabling analog to digital conversion early in the signal processing chain.

18 Claims, 7 Drawing Sheets

(51) Int. Cl.
  *A61B 8/00* (2006.01)
  *G01S 15/89* (2006.01)
  *A61B 8/06* (2006.01)
  *H03M 3/00* (2006.01)

(52) U.S. Cl.
  CPC ............ *A61B 8/488* (2013.01); *A61B 8/5207* (2013.01); *G01S 7/5208* (2013.01); *G01S 7/52025* (2013.01); *G01S 7/52038* (2013.01); *G01S 7/52077* (2013.01); *G01S 7/52092* (2013.01); *G01S 15/8915* (2013.01); *G01S 15/8925* (2013.01); *A61B 8/48* (2013.01); *G01S 15/8993* (2013.01); *H03M 3/458* (2013.01)

(58) Field of Classification Search
  CPC ............. G01S 7/52025; G01S 15/8915; G01S 15/8925; G01S 7/52077; G01S 7/52038; G01S 15/8993; G01S 7/00; A61B 8/06; A61B 8/08; A61B 8/5207; A61B 8/42; A61B 8/065; A61B 8/488; A61B 8/48; H03M 3/458
  See application file for complete search history.

(56) References Cited

U.S. PATENT DOCUMENTS

| | | | |
|---|---|---|---|
| 5,997,479 A | 12/1999 | Savord et al. | |
| 6,013,032 A | 1/2000 | Savord | |
| 6,218,972 B1 | 4/2001 | Groshong | |
| 6,283,919 B1 | 9/2001 | Roundhill et al. | |
| 6,419,632 B1 * | 7/2002 | Shiki | A61B 8/06 600/443 |
| 6,443,896 B1 | 9/2002 | Detmer | |
| 6,458,083 B1 | 10/2002 | Jago et al. | |
| 6,530,885 B1 | 3/2003 | Entrekin et al. | |
| 6,623,432 B2 | 9/2003 | Powers et al. | |
| 6,693,573 B1 | 2/2004 | Linder | |
| 9,289,191 B2 * | 3/2016 | Clingman | A61B 5/0035 |
| 9,314,820 B2 * | 4/2016 | Akiyama | G01N 29/2418 |
| 10,285,595 B2 * | 5/2019 | Zalev | A61B 5/0095 |
| 2005/0111683 A1 * | 5/2005 | Chabries | H04R 25/356 381/317 |
| 2005/0251041 A1 | 11/2005 | Moehring | |
| 2008/0284628 A1 | 11/2008 | Willig et al. | |
| 2009/0036761 A1 * | 2/2009 | Abreu | A61B 5/14546 600/318 |
| 2009/0082673 A1 * | 3/2009 | Lu | B06B 1/0622 600/459 |
| 2010/0271188 A1 * | 10/2010 | Nysen | G06K 7/0008 340/10.41 |
| 2012/0197126 A1 * | 8/2012 | Hashiba | G01S 15/8963 600/443 |
| 2012/0272738 A1 * | 11/2012 | Klessel | G01S 7/52085 73/602 |
| 2013/0116538 A1 * | 5/2013 | Herzog | A61B 6/4405 600/407 |
| 2013/0197346 A1 * | 8/2013 | Milner | A61B 5/0275 600/409 |
| 2013/0281819 A1 * | 10/2013 | Schmid | A61B 8/4281 600/407 |
| 2015/0297090 A1 * | 10/2015 | Herzog | A61B 6/4405 600/407 |
| 2018/0070830 A1 * | 3/2018 | Sutin | A61B 5/0075 |

OTHER PUBLICATIONS

Norman; NPL, (A Band-Pass Delta-Sigma Modulator for Ultrasound Imaging at 160 MHz Clock Rate, IEEE journal of solid-state circuits, vol. 31, No. 12, Dec. 1996) (Year: 1669).*

Qin et al "A 1.8 CMOS Fourth-Order Gm-C Bandpass Signa-Delta Modulator Dedicated to Front-End Ultrasonic Receivers" Analog Integrated Circuits and Signal Processing, vol. 48, No. 2, May 9, 2006 p. 121-132.

Norman O: "A Band-Pass Delta-Sigma Modulator for Ultrasound Imaging at 160 MHzclock Rate",IEEE Journal of Solid-State Circuits, IEEE Service Center, Piscataway, NJ, USA, vol. 31, No. 12,Dec. 1, 1996 (Dec. 1, 1996), pp. 2036-2041.

* cited by examiner

ULTRASOUND IMAGING SYSTEM PROBE AND SYSTEM, AND AN IMAGING METHOD This application is the U.S. National Phase application under 35 U.S.C. § 371 of International Application No. PCT/EP2016/080409, filed on Dec. 9, 2016, which claims the benefit of EP Application Serial No. 15198841.7, filed Dec. 10, 2015. These applications are hereby incorporated by reference herein.

FIELD OF THE INVENTION

This invention relates to an ultrasound imaging system probe and the whole system, and an imaging method. It relates in particular to the analogue to digital converter circuits used in such imaging applications.

BACKGROUND OF THE INVENTION

Harmonic ultrasound imaging is one particular type of ultrasound imaging technique which is gaining increased interest. It exploits non-linear propagation of ultrasound through the body tissues. The high pressure portion of the wave travels faster than low pressure portions resulting in distortion of the shape of the wave. This change in waveform leads to generation of harmonics (multiples of the fundamental or transmitted frequency) from the tissue. For example, it is known to use the second harmonic to produce the image as the subsequent harmonics are of decreasing amplitude and hence insufficient to generate a proper image.

The harmonic waves that are generated within the tissue increase with depth to a point of maximum intensity and then decrease with further depth due to attenuation. Hence the maximum intensity is achieved at an optimum depth below the surface.

Harmonic imaging is based on the transmission of a relatively low frequency ultrasound waves that enable high penetration; and reception of one or more of the harmonics of the transmitted signal that appear in the reflections due to different scatterers. In this way, a higher penetration depth can be combined with higher special resolution than is achievable for higher frequencies.

Harmonic imaging has very broad and increasing applications. It is used in classical ultrasound imaging to obtain better special resolution with low frequency (e.g. 2.5 to 6 MHz) ultrasound. It becomes an even more interesting imaging method when higher frequencies are used, because the existing methods become proportionally more complex and costly. Especially, the low penetration depth of high-frequency ultrasound requires imaging techniques that can circumvent this problem.

In addition to classic imaging applications, harmonic imaging can play an important role in applications like tissue characterization where it can enable accurate differentiation between different tissues by providing accurate amplitude measurements at a certain frequency or a combination of frequencies. The fine amplitude and frequency resolution can provide information about tissues, boundaries and anomalies.

A problem with ultrasound imaging systems is the signal to noise of the received information. This is improved by providing earlier analog to digital conversion (for a digital signal, connectivity and signal processing are more robust to noise and interference) but this gives rise to higher power consumption of the receiver circuitry.

The article "A 1.8V CMOS fourth-order Gm-C bandpass sigma-delta modulator dedicated to front-end ultrasonic receivers" in Analog Integrated Circuits and Signal Processing, vol. 48, no. 2, 9 May 2006 pages 121-132 (XP 019390181) discloses an ultrasonic receiver which makes use of a band-pass sigma delta converter, so that the receiver can be tuned to different frequencies.

SUMMARY OF THE INVENTION

The invention is defined by the claims.

According to examples in accordance with an aspect of the invention, there is provided an ultrasound imaging system probe, comprising:

an imaging transducer head arranged to transmit an ultrasound signal at a transmitted ultrasound frequency; and a reception circuit for processing received reflected ultrasound signals, wherein the reception circuit comprises an analogue to digital sigma delta converter which comprises a closed loop which comprises a tunable band pass filter with tunable center frequency and bandwidth, and wherein the center of the pass band of the tunable band pass filter is tunable between a first frequency which corresponds to the transmitted ultrasound frequency and a second frequency which corresponds to a desired harmonic of the transmitted ultrasound frequency.

The invention thus makes use of band-pass sigma-delta ADCs. There may be one or more analog to digital sigma delta converters. These are devices from an emerging technology that is primarily driven by applications like software defined radios, where this type of converter can provide the required flexibility and programmability of the architecture. A programmable center frequency is provided, and the pass band is selected by the ultrasound acquisition electronics. Further, the pass band and the center frequency may be accurately tuned for example between the transmitted signal frequency or the desired harmonic of the transmitted signal such that the ADC can be effectively positioned to process only the desired frequency band. This can be done by introducing band pass tuning circuitry that uses as a reference the known transmit frequency or its harmonics. The probe may have very high frequency selectivity and very high amplitude resolution based on the programmable band pass filter incorporated in the ADC closed (feedback) loop. The analog to digital converter may also have programmable clock frequency and DAC scalability.

The band-pass conversion aims to optimize energy usage by converting only the desired frequency band.

The center of the pass band of the tunable band pass filter may thus correspond to a transmitted ultrasound frequency or a desired harmonic of the transmitted ultrasound frequency. The band-pass conversion impacts the achievable signal to noise ratio because the noise outside the band no longer influences the operation. This enables the system to zoom in a band with higher resolution without chaining the noise performance for the building blocks of the ADC.

The transducer head may comprise an array of transducer elements, and wherein the signal processing circuit comprises an analogue to digital sigma delta converter for each transducer element of the transducer head or for a group of transducer elements. In this way, there is digitization at the level of the individual transducer elements.

The reception circuit may then comprise an amplifier between each transducer element and the respective analog to digital sigma delta converter.

The band pass filter may be tunable between a low resolution high bandwidth mode and a high resolution low bandwidth mode. These two modes then correspond to different imaging modes for the ultrasound imaging system in which the probe is used.

The band pass filter may be further tunable to a medium resolution medium bandwidth mode. There are then at least three different imaging modes.

The invention also provides an ultrasound system comprising:
an ultrasound imaging system probe as defined above;
a controller for controlling the probe;
a beamformer; and
a signal processing circuit for processing the signals from the reception circuit to generated an ultrasound image.

The ultrasound system may process received reflected ultrasound signals which are harmonics of the transmitted ultrasound signals.

The controller may be adapted to control the tunable band pass filter in synchronism with switching between different receiving operating modes of the ultrasound system. These receiving operating modes may define different resolution versus bandwidth options. Thus, the tuning of the band pass filter depends on the transmit frequency that is used as well as the receiving mode that is used.

Examples in accordance with another aspect of the invention provide an ultrasound imaging method, comprising:
providing ultrasound into a volume to be image using an imaging transducer head; and
processing received reflected ultrasound signals, by tuning a band pass filter within the closed loop of an analogue to digital sigma delta converter the band pass filter having a tunable center frequency and bandwidth,
wherein the method comprises setting the center of the pass band of the tunable band pass filter to the transmitted ultrasound frequency or a desired harmonic of the transmitted ultrasound frequency.

In addition, the pass band may be set to another center frequency or bandwidth. This might be required when the used transmission beamforming or signal type (e.g. chirp) results into the appearance of signal components in a different frequency band.

The transducer head may comprise an array of transducer elements, and wherein the method comprises performing analogue to digital conversion individually for each transducer element of the transducer head.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
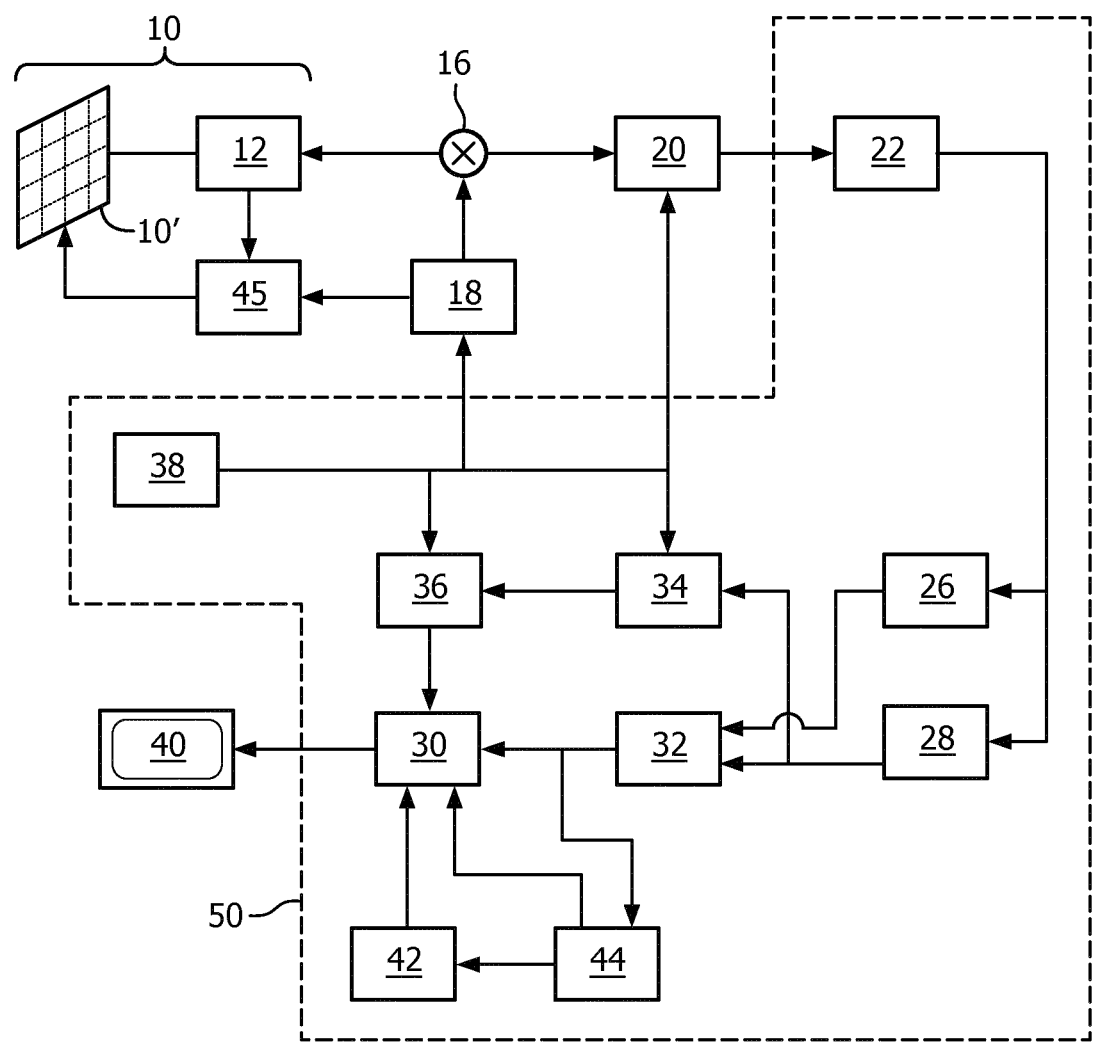
FIG. 1 shows a known ultrasound imaging system which may be modified to use the ultrasound probe design of the invention.

The invention provides an ultrasound imaging system probe which comprises an imaging transducer head and a reception circuit for processing received reflected ultrasound signals. The reception circuit comprises an analogue to digital sigma delta converter which comprises a closed loop which comprises a tunable band pass filter. This enables the analog to digital converter to process only the desired frequency band. The ADC conversion bandwidth and effective number of bits (ENOB) are in this way programmable giving a more efficient probe design, and also enabling analog to digital conversion early in the signal processing chain.

The general operation of an ultrasonic diagnostic imaging system will first be described, with reference to FIG. 1.

Note that the reception function of the system is in particular described below since this invention relates to the analog to digital conversion in the receive channel.

The system comprises an ultrasound probe 10 which has CMUT transducer array 10' for transmitting ultrasonic waves and receiving echo information. The transducer array 10' may alternatively comprise piezoelectric transducer elements formed of materials such as PZT or PVDF. The transducer array 10' is a one- or a two-dimensional array of transducer elements capable of scanning in a 2D plane or in three dimensions for 3D imaging.

The transducer array 10' is coupled to a (optional) microbeamformer 12 in the probe which controls reception of signals by the CMUT array cells or piezoelectric elements. Microbeamformers are capable of at least partial beamforming of the signals received by groups or "patches" of transducer elements as described in U.S. Pat. Nos. 5,997,479 (Savord et al.), 6,013,032 (Savord), and 6,623,432 (Powers et al.).

The microbeamformer 12 is coupled by the probe cable to a transmit/receive (T/R) switch 16 which switches between transmission and reception and protects the main beamformer 20 from high energy transmit signals when a microbeamformer is not used and the transducer array is operated directly by the main system beamformer. The transmission of ultrasonic beams from the transducer array 10 is directed by a transducer controller 18 coupled to the microbeamformer by the T/R switch 16 and a main transmission beamformer (not shown), which receives input from the user's operation of the user interface or control panel 38.

One of the functions controlled by the transducer controller 18 is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to a main receive beamformer 20 where the partially beamformed signals from individual patches of transducer elements are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducer elements of a transducer array can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed taking into account the characteristics of the transmission beamformer. .In FIG. 1 only the receiver beamformers 12, 20 are shown, since this invention relates to the reception signal processing channel. In the complete system, there will also be a transmission chain with a transmission micro beamformer, and a main transmission beamformer.

The function of the micro beamformer 12 is to provide an initial combination of signals in order to decrease the number of analog cables. This is typically performed in the analog domain.

The final beamforming is done in the main beamformer 20 and is typically after digitization.

The transmission and reception channels use the same transducer array 10' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

For instance, the wall filter can be set to have a pass band characteristic which passes signals of relatively low amplitude from higher velocity materials while rejecting relatively strong signals from lower or zero velocity material. This pass band characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasonic image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 10' and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

This invention concerns the signal processing of the received reflected signals, and in particular it relates to the analog to digital conversion. Analog to digital band pass conversion early in signal processing path enables a more efficient probe design.

FIG. 1 shows the microbeamformer 12 and beamformer 20 before the signal processing path, and thus they operate in the analogue domain.

There are known approaches to perform the signal processing in a different way, and in particular the analog to digital conversion can be done before any beamforming is implemented. There are two different ultrasound imaging systems with earlier digitization as depicted in FIG. 2 and FIG. 3.

Figure 2:
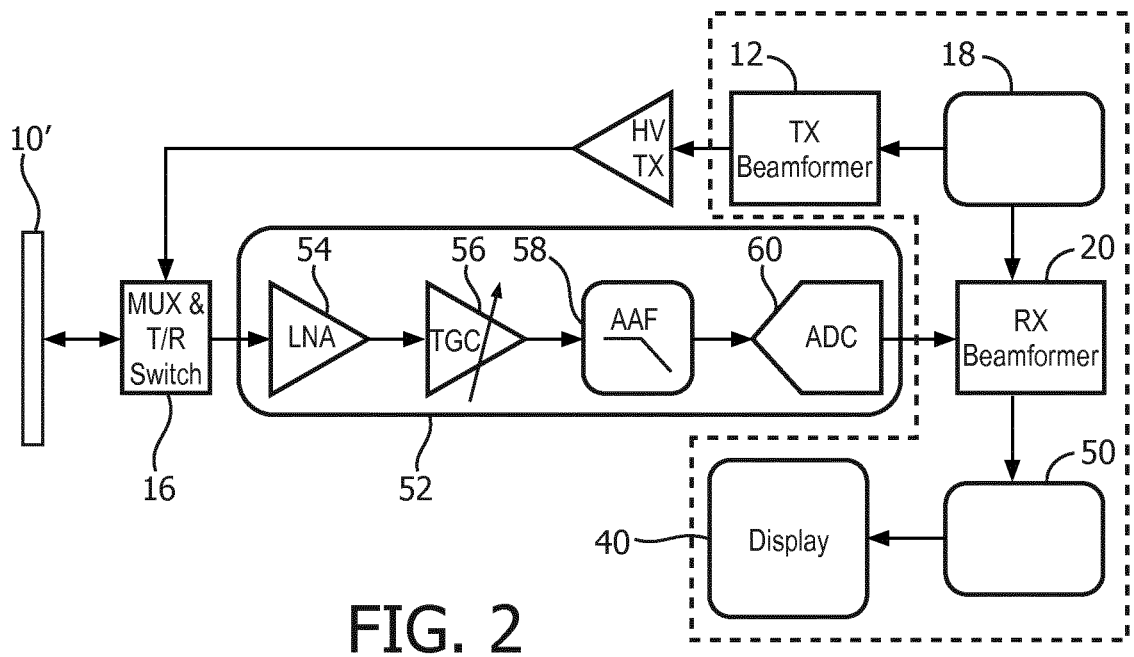
FIG. 2 shows in more detail a first known approach to the analog to digital conversion of the probe signals.

FIG. 2 shows the signal processing after the beamforming of the received signal as a single block 50. However, this represents the combination of the various units shown in FIG. 1 within the corresponding region 50.

In FIG. 2, the received signals are processed using an analog frontend 52 comprising a low noise amplifier (LNA) 54, a programmable time gain compensation (TGC) amplifier 56, and an anti-aliasing filter (AAF) 58 followed by an analog to digital converter 60. A transmit receive (T/R) switch 16 is shown which includes analog multiplexing so that analog multiplexers select groups of a reduced number of transducer elements to be connected to the beamformer. The selected group of elements is then electronically updated for each acoustic line. This approach is for example used in 2D ultrasound. It digitizes the signal before performing digital beamforming in the beamformer 20. The analog to digital conversion function is not performed in the probe itself. Instead, long and expensive cables are used to connect the signals to the backend. Element 54 is in the probe and there is a long cable between elements 54 and 56.

Figure 3:
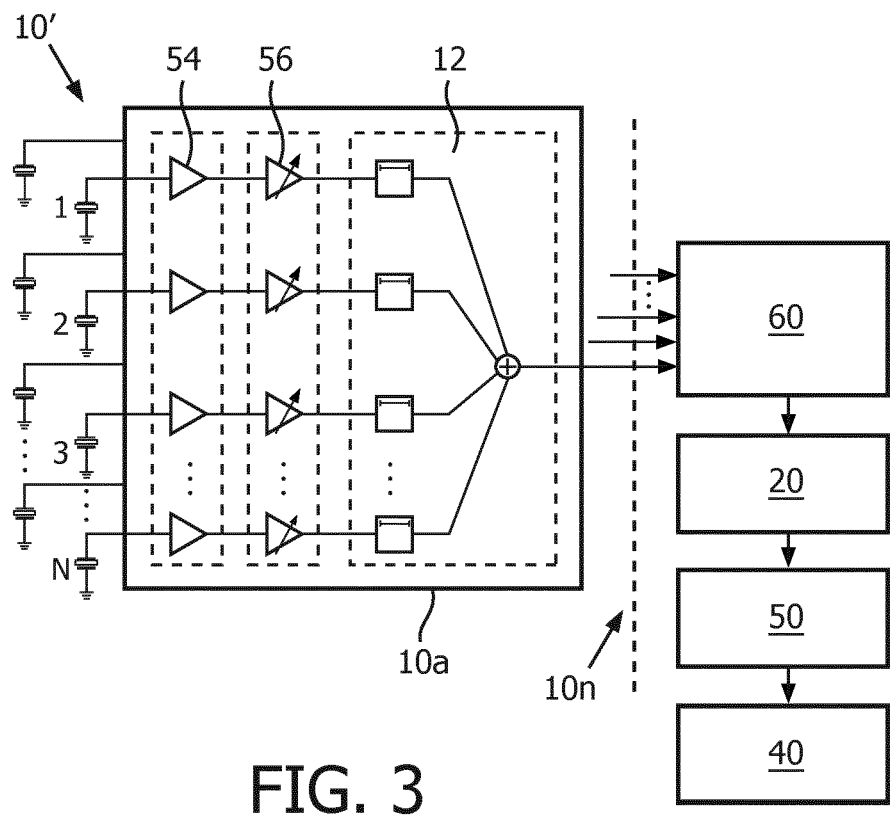
FIG. 3 shows in more detail a second example of known approach to the analog to digital conversion of the probe signals.

In FIG. 3, which shows an architecture typically used for 3D imaging, there is analog micro-beamforming on individual pixels of a group followed by digital beamforming for the group. As shown, the transducer elements of the transducer array 10' are divided into sub-arrays 10a . . . 10n. Within each sub-array, each transducer has a low noise amplifier (LNA) 54, and a programmable time gain compensation (TGC) amplifier 56 followed by a micro-beamformer 12 which operates in the analog domain. There is then summation of the signals for the sub-array, followed by analog to digital conversion using the analog to digital converter 60 followed by beam beamforming using the beamforming unit 20.

Ultrasound systems also differentiate on where the different functional blocks are located. In FIG. 2, for example, only part of the analog frontend 52 is typically implemented in the ultrasound probe. In contrast, the amplification, filtering, beamforming and controls are realized in a back-end system that is located in the scanner.

Furthermore, each system has a number of channels, each of which has a transmitter and a switch (including a diode bridge) that allows the passage of high voltage transmit pulses to the transducer elements, but blocks these pulses from reaching sensitive receivers. Echoes return to each receiver, which consist of amplifiers in series, including one that has a variable gain for TGC under user control. The output of each channel is passed on to the receive beamformer 20.

Pulse echo signals from the body are received by array elements and go through individual user-adjustable TGC amplifiers to offset the weakening of echoes by body attenuation and diffraction with distance. These signals then pass on to the receive beamformer 20.

Figure 4:
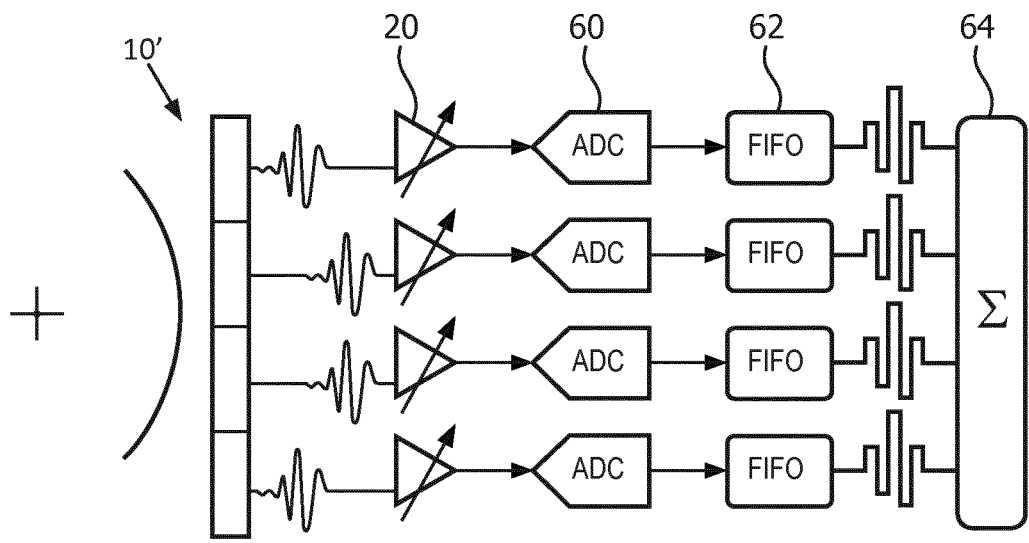
FIG. 4 shows in more detail a third example of approach to the analog to digital conversion of the probe signals.

FIG. 4 shows in schematic form a digitized highly parallel front-end. Each transducer element is coupled to an associated amplifier 20 which incorporates the time gain compensation (TGC) function. This approach provides early digitization of the received signal. The analogue to digital conversion may then be implemented in the probe, so that the connection cables are after the conversion to the digital domain.

The output from the amplifier 20 is digitized in analog to digital converter 60 before buffering in first in first out (FIFO) registers 62, which implement variable delays before summation in summer 64.

There are many benefits to use early digitization for many types of transducer configuration, including transducers for 3D imaging.

However, early digitization poses demanding requirements for the size and power consumption of the front-end electronics and the ADC function in particular. The requirements of the ADC function in terms of resolution such as the effective number of bits, ENOB, and conversion bandwidth, BW, can vary significantly from one mode of operation to another. ENOB and BW are the two most important parameters that are determined by the requirements of the particular application (imaging mode or key feature extraction from the imaging). These parameters also determine the requirements of the whole imaging system and detailed specifications of the individual building blocks.

Figure 5:
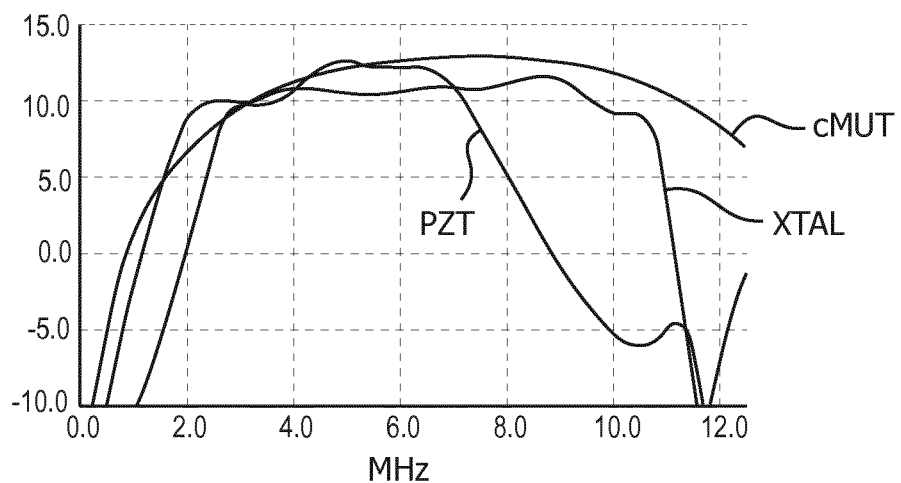
FIG. 5 shows how different ultrasound probe technologies, and in particular pressure-to-electrical conversion transducers, have different frequency characteristics.

In ultrasound imaging systems, the usable signal frequency band is determined by the frequency response of the ultrasound transduces. As illustrated in FIG. 5, different transducers operate in different frequency ranges (their acoustic performance varies with transmitted frequency). FIG. 5 shows the signal versus frequency for PZT, CMUT and crystal (XTAL) transducers.

A low frequency enables more penetration and a higher frequency enables improved tissue fill, finer detail and third harmonic imaging. Higher order harmonic imaging may be enabled by using broadband transducers or by using a narrowband transducer at the harmonic imaging frequency.

Figure 6:
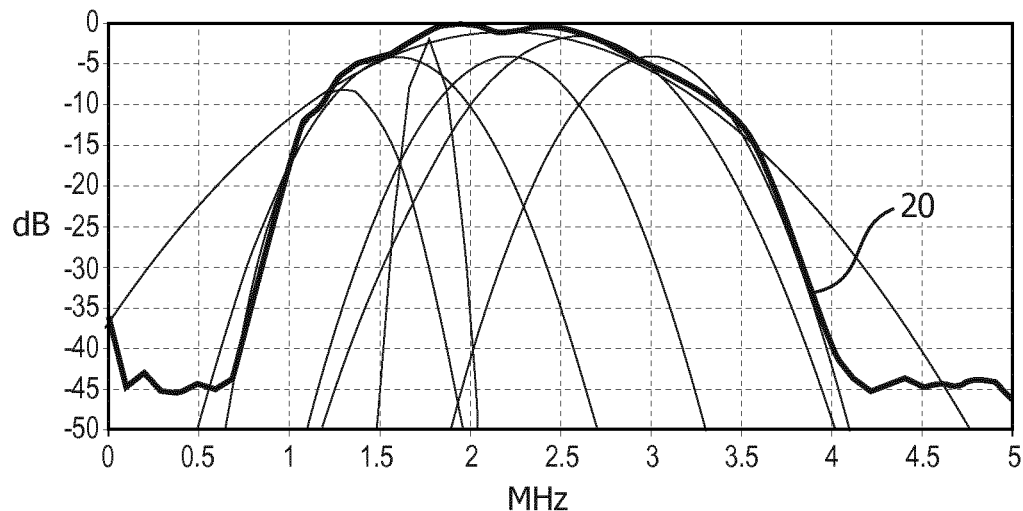
FIG. 6 shows how different operating modes may be used.

CMUT transducers have the broadest frequency band of operation. At the same time, the full frequency bandwidth is never used for all the time. In fact, most imaging modes use only parts of the total frequency band as shown in FIG. 6. FIG. 6 shows different frequency responses of the CMUT transducer for different imaging modes. The dark plot 20 shows a spectrum-live Doppler measurement mode. More details on the CMUT transducer frequency response for different imaging modes can be found in WO 2015/028945 A3.

The attenuation of ultrasound waves in the medium is an essential factor affecting the configuration of the front-end electronics. Ultrasound waves attenuate on a logarithmic scale rather than a linear scale.

This invention is based on the recognition that an adaptable band-pass signal processing approach may be used to adapt the bandwidth and the resolution of each measurement according to the requirements of each imaging mode.

Conventional ADCs are low pass, meaning that they can convert signals located between DC and a frequency $F_N$, where $F_N$ is the Nyquist frequency of the system.

Figure 7:
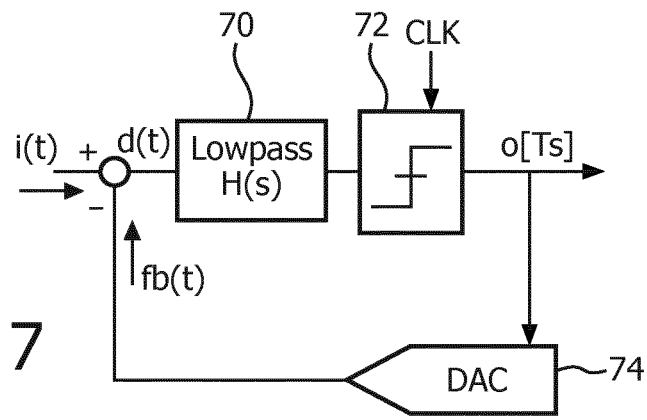
FIG. 7 shows a known sigma delta analog to digital converter.

FIG. 7 shows the structure of a Sigma-Delta ADC suitable for ultrasound image processing.

The analog input i(t) is low pass filtered in filter 70 before being clocked by a 1 bit analogue to digital converter 72 to generate the digital output o[Ts]. A feedback path includes a 1 bit digital to analogue converter 74, and the analogue feedback signal fb(t) is combined with the input to derive a difference signal d(t) which is supplied to the low pass filter 70.

Note that multi-bit ADC and DACs may instead be used in the feedback loop.

Figure 8:
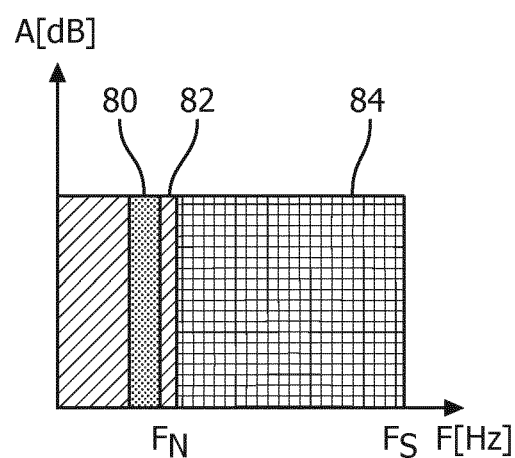
FIG. 8 shows the frequency characteristics of output signal of the converter of FIG. 7.

FIG. 8 shows the desired signal band 80, the Nyquist frequency 82 and the oversampled frequency band 84.

This converter, in its classical low-pass operation, converts a rather large signal bandwidth that can exceed several times the bandwidth of the desired input signal. Further, the accuracy that can be achieved largely depends on how big is the conversion bandwidth. Obviously, in cases when the desired signal is in a narrowband at high frequency, both converters become very inefficient in terms of power consumption and performance and on top of that produce a lot of data that is not useful for proper image construction.

Figure 9:
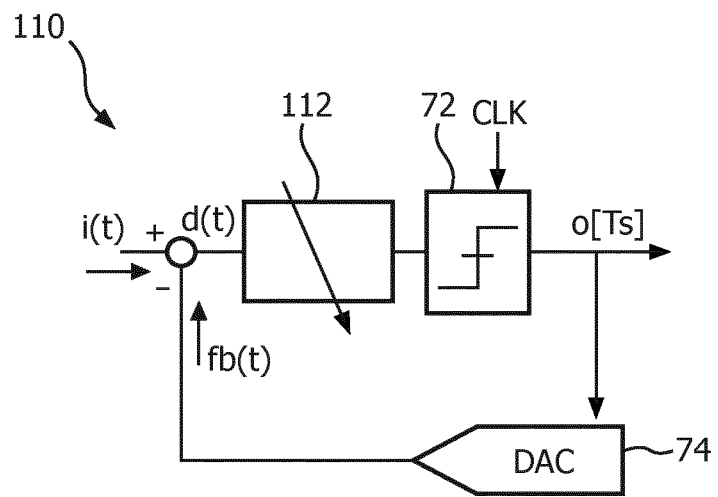
FIG. 9 shows a tunable sigma delta analog to digital converter for use in an ultrasound probe of the invention.

FIG. 9 shows an analog to digital converter 110 which is modified in accordance with the invention. The analog input i(t) is filtered in filter 112 before being quantized in amplitude and time by the 1 bit analogue to digital converter 72 (as also in FIG. 7) to generate the digital output o[Ts]. A feedback path includes a 1 bit digital to analogue converter 74, and the analogue feedback signal fb(t) is combined with the input to derive a difference signal d(t) which is supplied to the filter 112.

As explained above, in the general case, the ADC and the DAC in the closed loop may be multi-bit.

The analog to digital converter may have a programmable clock frequency and DAC scalability.

The clock frequency may be adjusted in order to achieve the following benefits:

(i) it can be increased to increase the resolution in the conversion pass band, by effectively increasing the oversampling ratio for this band (ii) it can be decreased in order to save power (thereby to sacrifice some resolution when not needed)

(iii) it can be used also to tune the system. The system operation is a result of the interaction of the loop filter with the clock frequency. When it is difficult to implement the exact desired value for the loop filter coefficient, the overall desired performance can be still achieved by adapting the clock frequency.

A fixed clock frequency may be preferred for a simplified implementation of the whole system.

The DAC may be rescaled if the clock frequency changes, in order to assure the same DAC output with the new clock. Furthermore, the DAC can be scaled to accommodate different maximum input signals.

The filter 112 is a tunable band pass filter. In order to realize optimal position of the pass-band, the filter programmability can be controlled by synchronization signals derived from the transmit signals used for the particular imaging mode. This enables further optimization of the overall signal processing chain and simplifies the design of the converter.

Most classic modes such as the brightness mode (B-mode or 2D mode) and the Doppler mode may use the proposed principle which brings the benefit of converting only the desired bandwidths.

In addition, harmonic imaging modes in which the transmission and reception uses the same transducer array can be employed (e.g. for a given frequency). For example, the transmitter transmits the signal with the low ⅓ of the frequency band of the transducer, while receiver works in the upper ⅓ of the frequency band to capture the $3^{rd}$ harmonic of the transmitted signal.

In addition, the transmission uses the whole band of one low frequency transducer while the receiver uses another high-frequency transducer with a reception band located at 3× higher frequencies.

Figure 10:
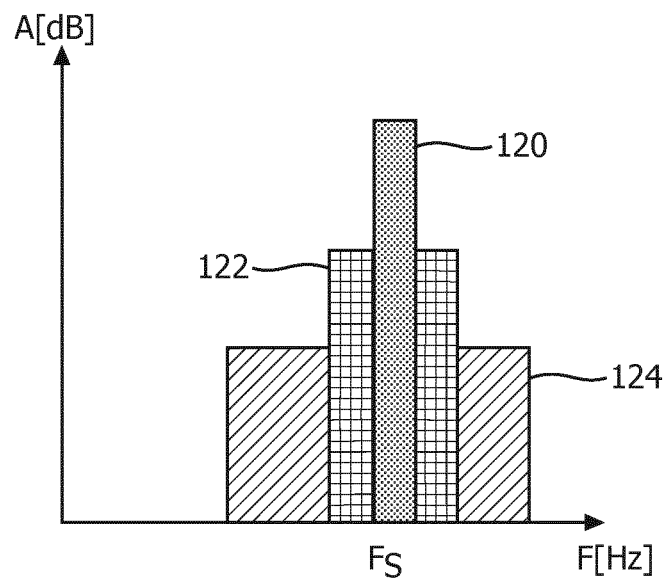
FIG. 10 shows the frequency characteristics of the converter of FIG. 9 in three different operating modes.

FIG. 10 shows the pass band of the filter 112 and the conversion band of the complete ADC. The region 120 shows a narrow band very high resolution mode, for example greater than 100 dB with a bandwidth of 200 kHz. This enables very accurate amplitude measurements in a narrow frequency band for tissue characterization.

The region 122 shows a moderate band and resolution mode, for example greater than 80 dB with a bandwidth of 1 MHz. The region 124 shows a broad band low resolution mode, for example greater than 50 dB with a bandwidth of 3 MHz.

Thus, the band pass filter may be tunable between a low resolution high bandwidth mode and a high resolution low bandwidth mode. The high bandwidth mode for example has a pass band of more than 1 MHz, for example more than 1.5 MHz and possibly more 3 MHz, whereas the low/narrow bandwidth mode has a pass band of less than 1 MHz, for example less than 750 kHz, for example less than 500 kHz and possibly less than 250 kHz. The y-axis in FIG. 10 illustrates the achievable dynamic range (DR) of the complete A/D converter. Typically the dynamic range is used to derive the resolution in terms of Effective Number of Bits (ENOB). ENOB=(SNR-1.76)/6.04 where in the ideal case SNR (signal to noise ratio)=DR.

The center frequency of the pass band is tuned to the transmit frequency or to a harmonic of the transmit frequency. There are many options for the transmit frequency. Typically diagnostic imaging uses 2 MHz to 5 MHz, however for in-body imaging with catheters, frequencies of 30 MHz or higher can be used. For microvascular structures, ever higher frequencies may be employed.

Adjusting the center frequency of the analog to digital converter is carried out at a circuit level. The band pass filter is for example realized with a combination of active and passive circuits. These can be used to adapt the center frequency and the pass-band of the filter to the various modes outlined above. These modes are discussed further below.

The narrow bandwidth mode, for ultrasound acquisition below 1 MHz can have bandwidth as narrow as a few tens of kHz e.g. 100 kHz. The corresponding high resolution refers to the Dynamic Range (DR) and Signal to Noise Ratio (SNR) of the acquisition electronics. They are considered high resolution if they exceed the values for classical B-mode imaging which are below 12 bit Effective number of bits (ENOB). The primary need for the narrow band acquisition is driven by the subtle difference between different tissues that result in characteristic narrow band reflections that can only be analyzed with high accuracy and power efficiency with a narrow band signal acquisition. This mode is for example used for Doppler imaging (continuous and pulsed).

The medium bandwidth mode is for example for harmonic imaging, in which the ADC center frequency is at a harmonic of the transmission frequency. The benefit for harmonic imaging is in the fact that when higher frequency signals are more attenuated, more gain is need to acquire them. Applying gain only for these frequencies will require analog pre-filtering in order to avoid clipping from the stronger lower frequencies signals. Analog filtering is typically expensive either in area or in power.

The large bandwidth mode is for example for B-mode or A-mode 2D and 3D imaging. The bandwidth is set to match the bandwidth of the ADC transducer.

The three modes can be seen as completely independent but they may for example be used in a sequence. Which mode to use will depend on the application or the measurement within the application.

For example, in a pregnancy scan, B-mode imaging can be used for general imaging while Doppler imaging can used for a particular measurement of blood flow e.g. in the fetus heart. Enabling the implementation of both modes in one ultrasound front-end provides efficiency and cost savings. Tissue characterization can again be a completely independent measurement that is used outside the body for better characterization of tissues or tissues boundaries, or inside the body (for example usage on catheters).

An imaging procedure might thus include initial usage of B-mode imaging (large bandwidth lower resolution acquisition) which is then followed by harmonic imaging with a higher resolution, and finally completed with a measurement type of image acquisition with maximum accuracy (as achievable in using the narrow bandwidth mode). This is useful when the data from the initial lower resolution imaging modes is used to guide the more refined modes, for example by narrowing the volume that has to be imaged with very high accuracy.

There are various ways to switch between the modes. One approach is for the three modes to be sequentially executed and only a few parameters are required to pass from one mode to the next. Alternatively, the modes can be interleaved. For example, after scanning a small volume in the B-mode, Doppler or Tissue characterizations are used to assess deeper the results or to provide input to a subsequent B-mode acquisition.

Figure 11:
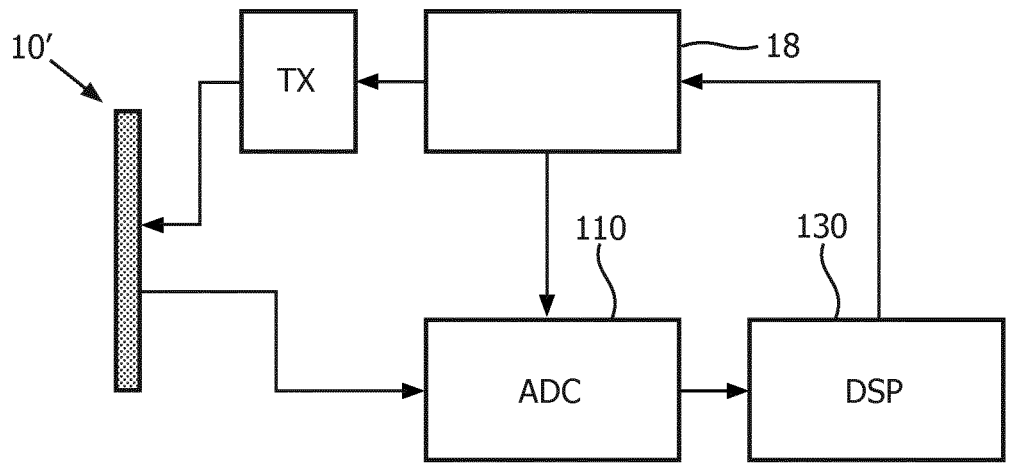
FIG. 11 shows a control circuit for controlling the tuning of the tunable sigma delta analog to digital converter of FIG. 9.

FIG. 11 shows a control circuit for controlling the pass band of the filter of the converter 110. The output of the filter is provided to a DSP 130 which controls the transducer controller 18. Synchronization signals from the transducer controller 18 are used to control the filter.

The DSP block 130 takes account of which signals have been used for transmission (the frequency and bandwidth) and the desired imaging mode (which determines which frequency bands have to be converted). In this case, the DSP 130 needs to tune the analog band pass filter in the loop such that it is centered in the desired conversion bandwidth. There are known approaches for how to tune the analog filter response using, as a reference, a fixed known frequency (e.g. the main frequency component of the transmission signal).

The different modes of operation are enabled by design by introducing programmability of the filter coefficients (the unity gain frequency of the integrators and the values of the feedforward and the feedback coefficients in the loop filters shown in the figures). The preferred way to implement programmability will depend on the design of the filter. In the case of active resistor-capacitor (RC) or transconductance-capacitor (Gm-C) filters that are typically preferred, the coefficients are realized by selecting proper values for the resistors, capacitors and the transconductance values.

For example, for the topologies of FIGS. 12 and 13 (described below) the center frequency is determined by the unity gain frequency of the integrators and the local feedback paths.

In order to vary the center frequency of the filter to a desired harmonic, all coefficients should be scaled. Typically for a fixed clock all coefficients are scaled with identical scale factor N, which is pre-calculated. In addition, for each coefficient, at least two values are implemented in the hardware: a nominal value and N times the nominal value. For each new bandwidth a new value of N has to be used and hardware enabled during implementation.

If all coefficients are scaled with the same factor N, the center frequency changes but not the bandwidth. To adjust also the bandwidth, the different poles in the transfer function H(s) are scaled with a different factor. Again the scaling factor is pre-calculated and enabled in the hardware.

This scaling can be used for a fixed clock as long as the center frequency of the conversion is below fs/4 (fs is the sampling frequency). This requirement is needed in order to maintain the stability of the ADC. Further, similar to the poles, the zero of the transfer function H(s) (in the numerator of the transfer function) should be scaled with the same coefficients. The transmission frequency and its harmonics can thus be used for calibration of the nominal transfer function coefficients and the scaling factors N.

When this variable pass-band signal digitization is used in an ultrasound imaging system, a highly flexible and energy and area efficient construction is enabled.

The converter may be used in the system of FIG. 3 with analog beamforming. However, it enables a variety of new options if digitization is performed very early in the signal processing chain before any beamforming.

In particular the approach then addresses the following problems:

(i) Analog-to-digital conversion of a broad frequency range of a few MHz is very costly in terms of power and chip area. The cost depends also heavily on the resolution that is required such that broadband high accuracy converters (>13 ENOB) typically have hundreds of mW power consumption. In a band-pass configuration the power requirements decrease significantly with the decrease of conversion bandwidth.

(ii) Band-pass sigma delta converters are very flexible and the acquisition front-end can be adapted electronically, with a few configuration bits, to operate from a very narrow band mode (e.g. a few kHz for CMUT base imaging) to the full CMUT bandwidth. This can be done very quickly, even without adaptation of the CMUT bias voltages thus increasing re-configuration speed and avoiding bias switching artifacts.

(iii) Band-pass acquisition, naturally limits the amount of data because only the frequency range that is needed by the particular imaging modality is actually acquired. The non-desired noise band can be easily filtered with simple digital filters. This further simplifies the requirements towards the complete system and decreases its power consumption and cost.

In contrast to classical analog band-pass acquisition, where analog band-pass filters are used, the proposed implementation has the advantages of much higher speed. Analog band-pass filters are usually rather slow as they need settling time for each consecutive signal acquisition. In band-pass sigma delta converters, the settling process is occurring at start-up and during normal operation the built-in filter operates from a steady-state mode and thus reacts very quickly to input signal changes.

The implementation is also much more stable. As analog band pass filter typically incorporate resonators or other filters with positive feedback they are very prone to instabilities, especially higher order filters. In a band pass sigma delta architecture, the stability is guaranteed via the existing negative feedback loop and the filter construction may guarantee its stability.

The design is also more easily scalable and configurable. This originates from the several additional degrees of freedom that are introduced such as clock speed, DAC and quantizer programmability that enable very broad configurability of the bass-band center frequency and bandwidth.

The filter may be used to enable transmission at one frequency and detection at another with electronic front-end reconfiguration.

The filter 112 may be implemented in various ways.

Figure 12:
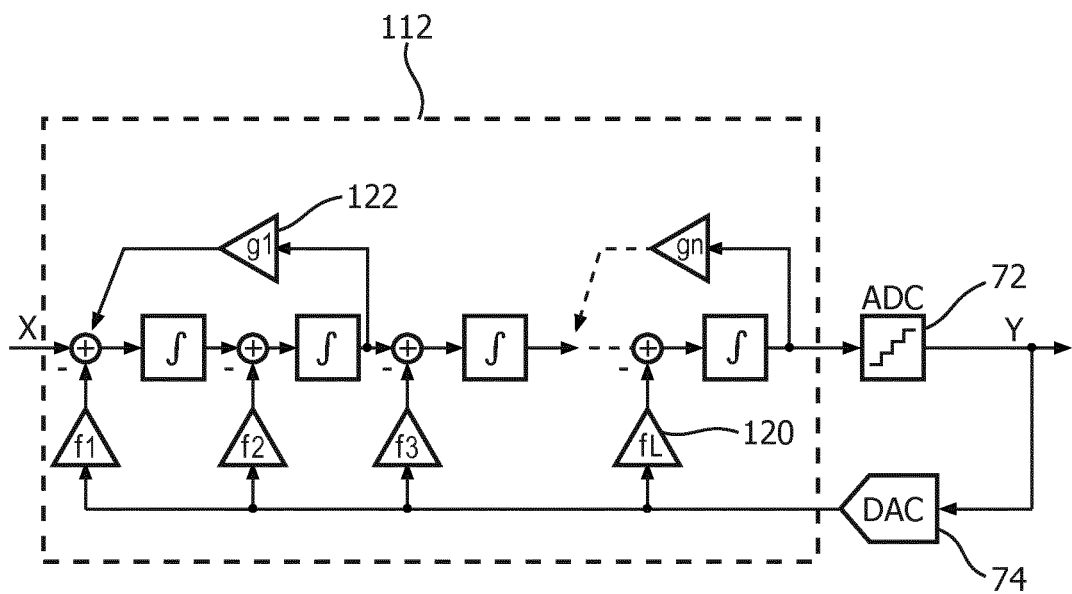
FIG. 12 shows the tunable sigma delta analog to digital converter of FIG. 9 with a first example of tunable band pass filter.

FIG. 12 shows an implementation of the circuit of FIG. 9 having a multi-level ADC 72 and DAC 74. The tunable band pass filter 112 has a feedback structure in which the analogue feedback signal is applied through first gain elements 120 with coefficient fx to addition nodes of the structure. Second gain elements 122 with coefficient gx are in feedback paths to the addition nodes. There are integrators between the nodes.

Figure 13:
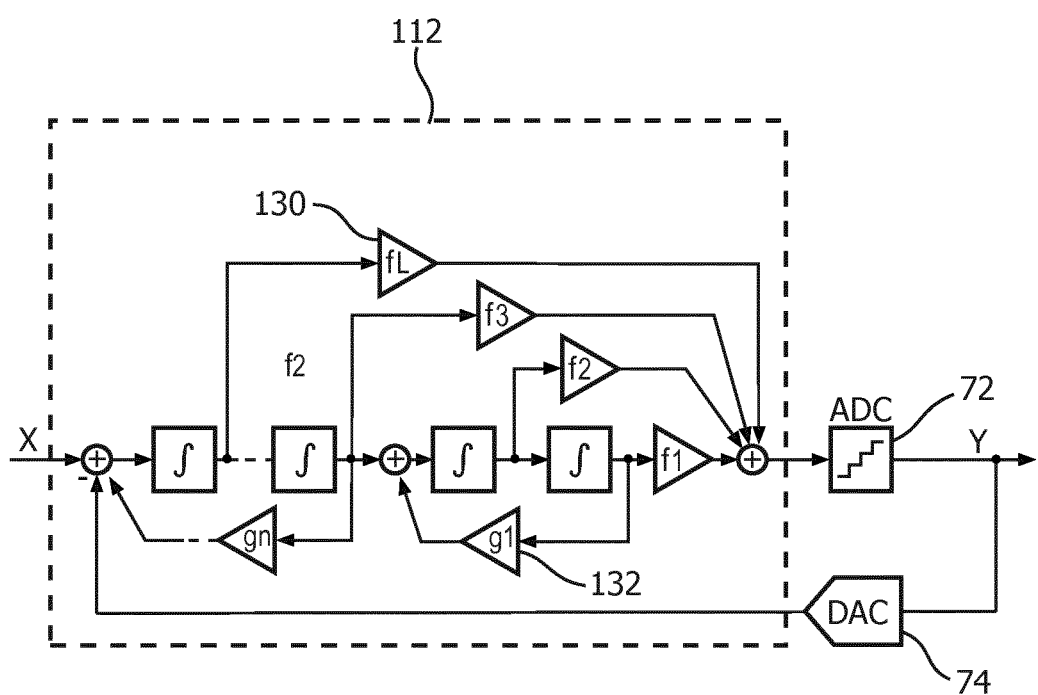
FIG. 13 shows the tunable sigma delta analog to digital converter of FIG. 9 with a second example of tunable band pass filter.

FIG. 13 shows an implementation of the circuit of FIG. 9 again having a multi-level ADC 72 and DAC 74. The tunable band pass filter 112 has a feed forward structure in which the analogue feedback signal is applied only to the first addition node of the structure. There are feedforward gain elements 130 with coefficient fx leading to a final addition node. There are also feedback gain elements 132 with coefficient gx leading to addition nodes of the structure. There are again integrators between the nodes.

These are just two known examples of possible programmable band pass filter structure which may be used within the converter. Other filter structures may also be employed.

The filters are programmable by making the fx and gx coefficients in the architectures programmable as described above By way of example, the link between the controller 18 and the analog to digital converter 110 (FIG. 11) may be a reference frequency signal that is used to adapt the fx and gx coefficients such that the frequency response of the filter is matched to the reference signal. This can be done, for example, by adapting the coefficients until the filter response to the reference signal is maximized.

There may be more than one reference signal from the controller 18 to the converter 110. The signals may be static for switching the filter to a pre-programmed known state, or they may be for adapting the filter to a reference signal. The reference signal may be time variable. A most simply implementation may have all modes enabled in hardware at design. The controller can then switch between modes and just calibrate if needed.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound imaging system, comprising:
a probe comprising:
an imaging transducer head arranged to transmit an ultrasound wave at a transmitted ultrasound frequency and receive reflected ultrasound echoes; and
a reception circuit for processing an analog signal associated with the received reflected ultrasound echoes,
wherein the reception circuit comprises an analog to digital sigma delta converter (sigma delta ADC), wherein the sigma delta ADC comprises an individual filter configured to filter the analog signal prior to the analog signal being converted to a digital signal, thereby reducing a power consumption of the sigma delta ADC such that the reception circuit is positioned within the probe,
wherein the individual filter comprises a tunable band pass filter with a tunable center frequency tunable between a first frequency and a different, second frequency, and
wherein the individual filter is configured to:
pass the first frequency of the signal when the tunable center frequency of the tunable band pass filter is tuned to the first frequency; and
pass the second frequency of the signal when the tunable center frequency of the tunable band pass filter is tuned to the different, second frequency.

2. A system as claimed in claim 1,
wherein the imaging transducer head comprises an array of transducer elements, and
wherein the reception circuit comprises a respective analog to digital sigma delta converter for each transducer element of the transducer head.

3. A system as claimed in claim 2, wherein the reception circuit comprises an amplifier between each transducer element and the respective analog to digital sigma delta converter.

4. A system as claimed in claim 1, comprising:
a controller for controlling the probe;
a beamformer; and
a signal processing circuit for processing the signal to generate an ultrasound image.

5. A system as claimed in claim 4, wherein the controller is adapted to tune at least one of the tunable center frequency or a tunable bandwidth of the tunable band pass filter based on an imaging mode of the ultrasound system.

6. A system as claimed in claim 5, wherein, to tune the at least one of the tunable center frequency or the tunable bandwidth based on the imaging mode, the controller is adapted to provide synchronization signals derived from transmit signals for the imaging transducer head to the tunable band pass filter, wherein the transmit signals correspond to the imaging mode.

7. A system as claimed in claim 4, wherein the signal is associated with received reflected ultrasound signals which are harmonics of the transmitted ultrasound wave.

8. A system as claimed in claim 1, wherein the second frequency is a harmonic of the transmitted ultrasound frequency.

9. A system as claimed in claim 1, wherein the tunable band pass filter has a tunable bandwidth and wherein the tunable band pass filter comprises:

first circuitry configured to tune the tunable bandwidth to a first bandwidth; and
different, second circuitry configured to tune the tunable bandwidth to a different, second bandwidth.

10. A system as claimed in claim 9, wherein the first circuitry is further configured to tune the tunable center frequency to the first frequency, wherein the first frequency and the first bandwidth correspond to a low resolution, high bandwidth mode of the tunable band pass filter.

11. A system as claimed in claim 9, wherein the second circuitry is further configured to tune the tunable center frequency to the second frequency, wherein the second frequency and the different, second bandwidth correspond to a high resolution, low bandwidth mode of the tunable band pass filter such that the tunable band pass filter is tunable between the low resolution, high bandwidth mode and the high resolution, low bandwidth mode.

12. A system as claimed in claim 11, wherein the tunable band pass filter is further tunable to a medium resolution, medium bandwidth mode corresponding to a third frequency of the tunable center frequency and a third bandwidth of the tunable bandwidth.

13. A system as claimed in claim 1, wherein the analog to digital sigma delta converter comprises a closed loop, wherein the closed loop comprising the tunable band pass filter, an analog to digital converter, and a digital to analog converter.

14. An ultrasound imaging method, comprising:
providing, using an imaging transducer head of a probe, an ultrasound wave at a transmitted ultrasound frequency into a volume to be imaged;
receiving reflected ultrasound echoes using the imaging transducer head; and
processing, using a reception circuit, an analog signal associated with the received reflected ultrasound echoes, wherein the reception circuit comprises an analog to digital sigma delta converter (sigma delta ADC) comprising an individual filter, wherein the processing comprises:
filtering the analog signal using the individual filter prior to the analog signal being converted to a digital signal, thereby reducing a power consumption of the sigma delta ADC such that the reception circuit is positioned within the probe, wherein the individual filter comprises a tunable band pass filter with a tunable center frequency tunable between a first frequency and a different, second frequency such that the filtering comprises:
passing, using the individual filter, the first frequency of the signal when the tunable center frequency of the tunable band pass filter is tuned to the first frequency; and
passing, using the individual filter, the second frequency of the signal when the tunable center frequency of the tunable band pass filter is tuned to the different, second frequency.

15. A method as claimed in claim 14, wherein the imaging transducer head comprises an array of transducer elements, and wherein the method comprises performing analog to digital conversion individually for each transducer element of the transducer head.

16. A method as claimed in claim 14, comprising tuning the tunable band pass filter based on transmit signals for the imaging transducer head, wherein the transmit signals correspond to an imaging mode of a plurality of imaging modes.

17. A method as claimed in claim 16, wherein the plurality of imaging modes comprise:
a low resolution, high bandwidth mode corresponding to tuning of the tunable center frequency to the first frequency and tuning of a tunable bandwidth of the tunable band pass filter to the first bandwidth; and
a high resolution, low bandwidth mode corresponding to tuning of the tunable center frequency to the second frequency and tuning of the tunable bandwidth to the second bandwidth.

18. A method as claimed in claim 17, wherein the plurality of imaging modes further comprise a medium resolution, medium bandwidth mode corresponding to tuning of the tunable center frequency to a third frequency and tuning of the tunable bandwidth to a third bandwidth.

* * * * *